United States Patent
Takamoto

(10) Patent No.: US 11,430,231 B2
(45) Date of Patent: Aug. 30, 2022

(54) EMOTION ESTIMATION DEVICE AND EMOTION ESTIMATION METHOD

(71) Applicant: Mitsubishi Electric Corporation, Tokyo (JP)

(72) Inventor: Shusaku Takamoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 0 days.

(21) Appl. No.: 17/415,292

(22) PCT Filed: Feb. 4, 2019

(86) PCT No.: PCT/JP2019/003854
§ 371 (c)(1),
(2) Date: Jun. 17, 2021

(87) PCT Pub. No.: WO2020/161768
PCT Pub. Date: Aug. 13, 2020

(65) Prior Publication Data
US 2022/0067412 A1    Mar. 3, 2022

(51) Int. Cl.
*G08B 23/00*    (2006.01)
*G06V 20/59*    (2022.01)
(Continued)

(52) U.S. Cl.
CPC ........... *G06V 20/597* (2022.01); *B60W 40/08* (2013.01); *B60W 50/14* (2013.01);
(Continued)

(58) Field of Classification Search
CPC ........... G06K 9/00845; G06K 9/00261; G06K 9/00281; G06K 9/00302; B60W 40/08;
(Continued)

(56) References Cited

U.S. PATENT DOCUMENTS 7,821,409 B2 *  10/2010  Ishida ................ G06K 9/00845
                                                                 340/576
2014/0114536 A1   4/2014  Kobana et al.
(Continued)

FOREIGN PATENT DOCUMENTS

JP    2016-71577 A    5/2016
JP    2017-100039 A   6/2017
(Continued)

OTHER PUBLICATIONS

International Search Report for PCT/JP2019/003854 dated Apr. 23, 2019.
(Continued)

*Primary Examiner* — Anh V La
(74) *Attorney, Agent, or Firm* — Sughrue Mion, PLLC; Richard C. Turner

(57) ABSTRACT

A facial information detecting unit detects facial information related to facial features of a driver of a vehicle. A physical information detecting unit detects physical information related to physical features of the driver. A driving capability estimating unit estimates a driving capability of the driver on the basis of the facial information and the physical information. A facial expression estimating unit estimates the facial expression of the driver on the basis of the facial information. An emotion estimating unit estimates the emotion of the driver represented by the degree of comfort and the degree of activeness on the basis of temporal changes in the driving capability of the driver and the facial expression of the driver.

8 Claims, 6 Drawing Sheets

(51) Int. Cl.
*B60W 60/00* (2020.01)
*G06V 40/16* (2022.01)
*B60W 40/08* (2012.01)
*B60W 50/14* (2020.01)

(52) U.S. Cl.
CPC ....... *B60W 60/0051* (2020.02); *G06V 40/167* (2022.01); *G06V 40/171* (2022.01); *G06V 40/174* (2022.01); *B60W 2040/0818* (2013.01); *B60W 2050/143* (2013.01); *B60W 2050/146* (2013.01); *B60W 2540/229* (2020.02)

(58) Field of Classification Search
CPC ............. B60W 50/14; B60W 60/0051; B60W 2040/0818; B60W 2050/143; B60W 2050/146; B60W 2540/229; B60W 2540/221; G06V 20/597; G06V 40/167; G06V 40/171; G06V 40/174; A61B 5/0033; A61B 5/4809; A61B 5/18; A61B 5/6893
USPC ............. 340/576, 575, 573.1, 436, 439, 438
See application file for complete search history.

(56) References Cited

U.S. PATENT DOCUMENTS

| 2014/0171752 | A1* | 6/2014 | Park ...................... A61B 5/165 600/301 |
| 2017/0105662 | A1 | 4/2017 | Silawan et al. |
| 2017/0108864 | A1* | 4/2017 | Wiklinska ......... B60W 60/0051 |
| 2017/0150930 | A1 | 6/2017 | Shikii et al. |
| 2019/0213429 | A1* | 7/2019 | Sicconi .................. G06F 3/016 |

FOREIGN PATENT DOCUMENTS

| JP | 2017-144222 A | 8/2017 |
| WO | 2013/008301 A1 | 1/2013 |

OTHER PUBLICATIONS

Written Opinion for PCT/JP2019/003854 dated Apr. 23, 2019.
Communication dated Feb. 22, 2022 from the Japanese Patent Office in Application No. 2020-570671.

* cited by examiner

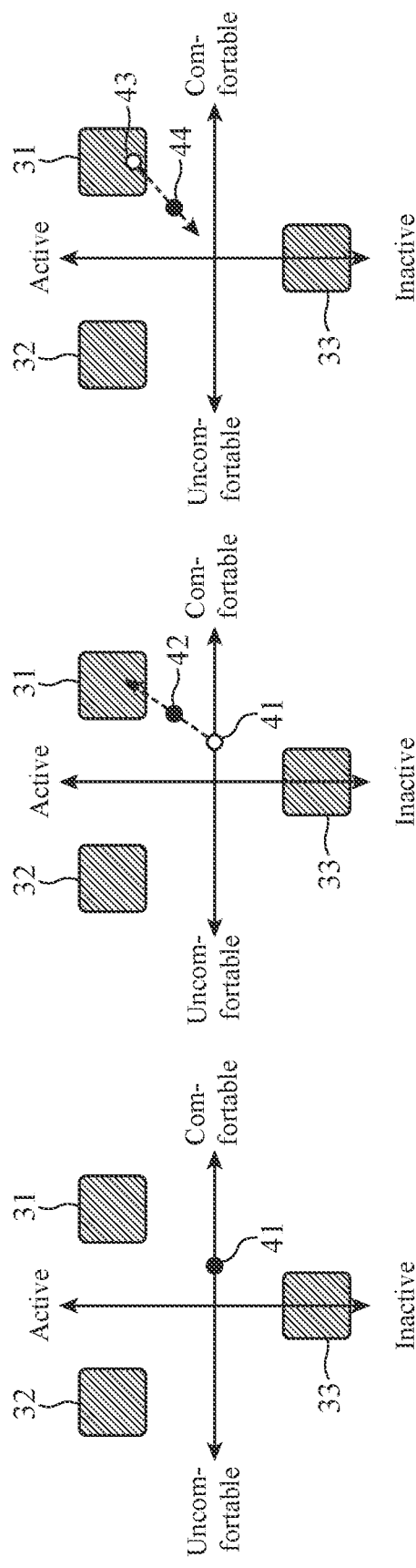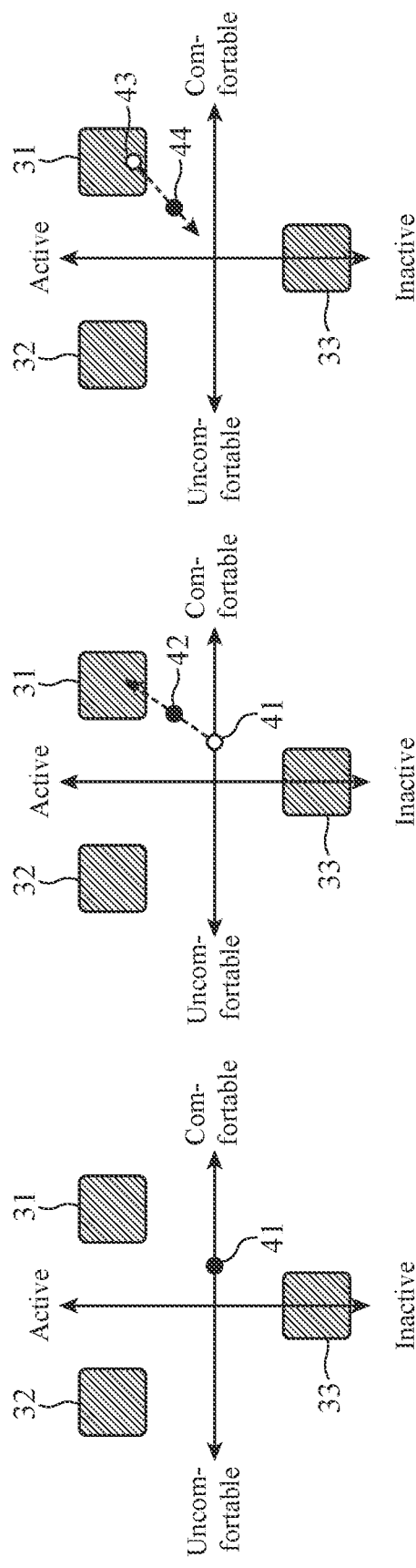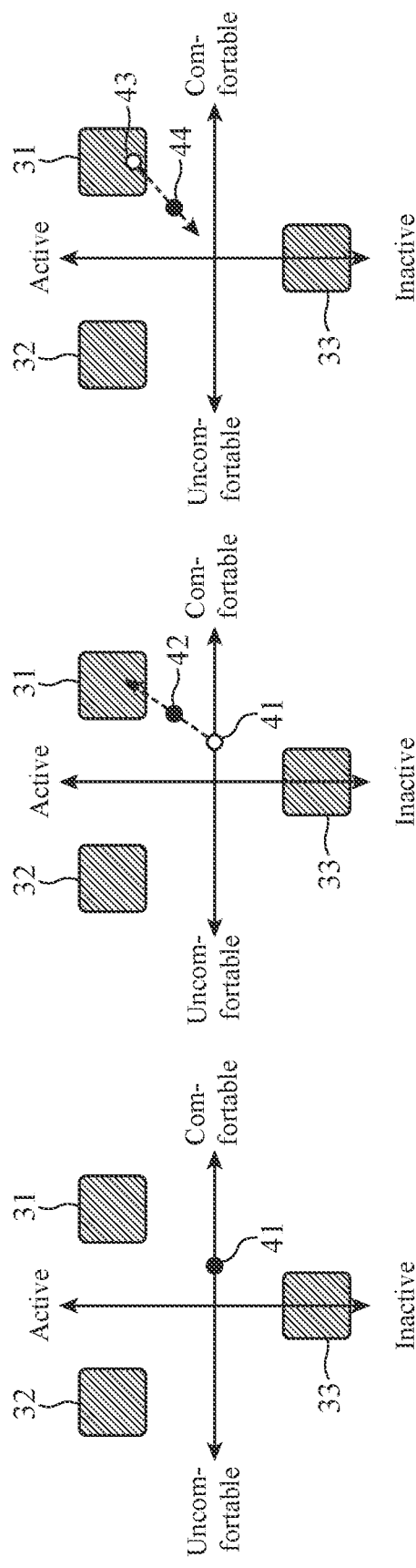

EMOTION ESTIMATION DEVICE AND EMOTION ESTIMATION METHOD

CROSS REFERENCE TO RELATED APPLICATIONS

This application is a National Stage of International Application No. PCT/JP2019/003854 filed Feb. 4, 2019.

TECHNICAL FIELD

The present invention relates to an emotion estimation device and an emotion estimation method for estimating an emotion of a driver.

BACKGROUND ART

Conventional emotion estimation devices detect physiological data and non-physiological data of a subject from, for example, an image captured by a camera, estimates the degree of awakening and the degree of comfort of the subject on the basis of the physiological data and the non-physiological data that have been detected, and selects an emotion that corresponds to the degree of awakening and the degree of comfort that have been estimated (see, for example, Patent Literature 1).

CITATION LIST

Patent Literature

Patent Literature 1: JP 2017-144222 A

SUMMARY OF INVENTION

Technical Problem

The emotions estimated by a conventional emotion estimation device are useful for predicting an action of a driver such as overspeed and road rage that may cause a traffic accident, thereby adjusting acceleration or deceleration by a driving assistance device, warning the driver, etc. However, since emotions have a duration, there is a disadvantage that emotions cannot be estimated correctly only by the degree of awakening and the degree of comfort.

The present invention has been made to solve the above-mentioned disadvantage, and an object of the present invention is to estimate emotions in consideration of temporal changes.

Solution to Problem

An emotion estimation device according to the present invention includes processing circuitry to detect facial information related to a facial feature of a driver of a vehicle, to detect physical information related to a physical feature of the driver; to estimate driving capability of the driver on a basis of the facial information and the physical information, to estimate a facial expression of the driver on a basis of the facial information, and to estimate an emotion of the driver represented by a degree of comfort and a degree of activeness on a basis of a temporal change in the driving capability of the driver and the facial expression of the driver.

Advantageous Effects of Invention

According to the present invention, since the emotions are estimated on the basis of temporal changes in the driving capability of a driver and in the facial expression of the driver, an emotion can be estimated in consideration of the temporal changes.

BRIEF DESCRIPTION OF DRAWINGS

FIGS. 4A, 4B, and 4C are graphs each illustrating an example of temporal changes of an emotion estimated by the emotion estimating unit of the first embodiment.

DESCRIPTION OF EMBODIMENTS

In order to describe the present invention further in detail, embodiments for carrying out the present invention will be described below with reference to the accompanying drawings.

First Embodiment

Figure 1:
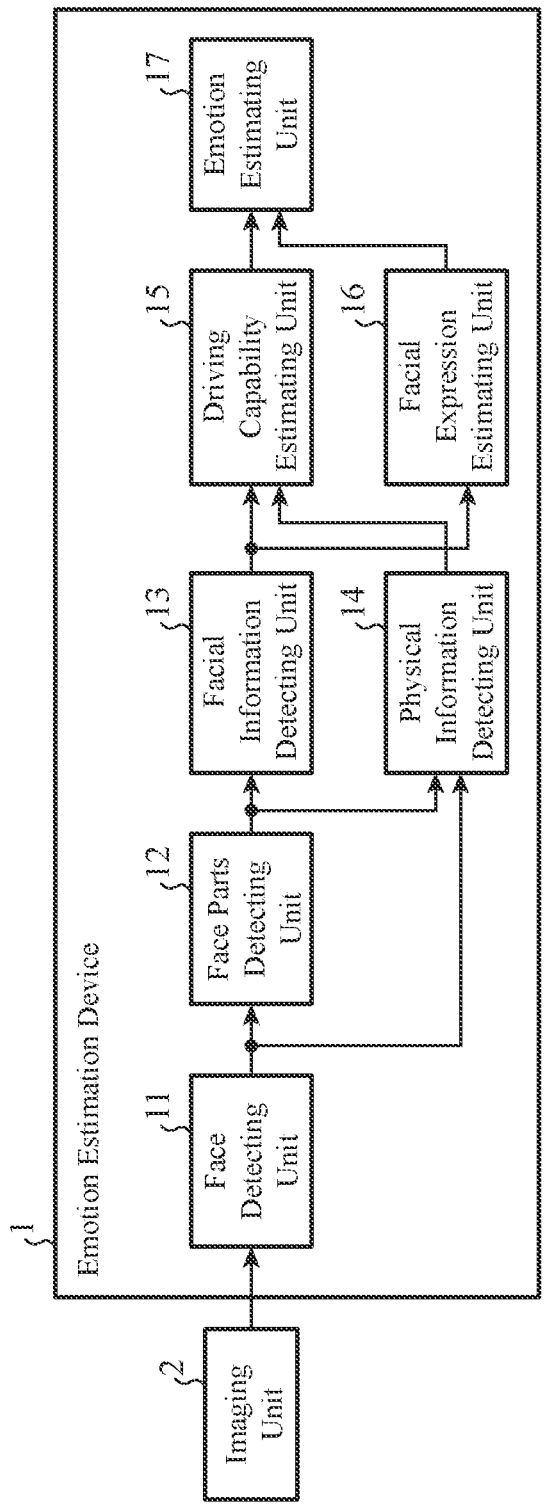
FIG. 1 is a block diagram illustrating an exemplary configuration of an emotion estimation device according to a first embodiment.

FIG. 1 is a block diagram illustrating an exemplary configuration of an emotion estimation device 1 according to a first embodiment. The emotion estimation device 1 according to the first embodiment is mounted on a vehicle or brought into a vehicle and estimates an emotion of a driver.

An imaging unit 2 is connected to the emotion estimation device 1. The imaging unit 2 is, for example, a camera installed near the steering wheel for capturing an image of the driver. The imaging unit 2 outputs a captured image capturing the driver to the emotion estimation device 1.

The emotion estimation device 1 includes a face detecting unit 11, a face parts detecting unit 12, a facial information detecting unit 13, a physical information detecting unit 14, a driving capability estimating unit 15, a facial expression estimating unit 16, and an emotion estimating unit 17.

The face detecting unit 11 acquires a captured image from the imaging unit 2. The face detecting unit 11 detects an area in which the driver's face is captured from the acquired captured image. The face detecting unit 11 outputs the face area of the captured image to the face parts detecting unit 12 and the physical information detecting unit 14.

The face parts detecting unit 12 detects face parts of the driver from the face area in the captured image detected by the face detecting unit 11. The face parts include the eyes, the nose, and the mouth. The face parts detecting unit 12 outputs the detected face parts to at least one of the facial information detecting unit 13 or the physical information detecting unit 14.

The functions of the face detecting unit 11 and the face parts detecting unit 12 are not necessarily included in the emotion estimation device 1 and may be included in an external device such as the imaging unit 2.

The facial information detecting unit 13 detects facial information related to the facial features of the driver on the basis of the face parts detected by the face parts detecting unit 12. The facial information includes at least one of the face orientation angle, the eye opening degree, the blinking speed, the mouth opening degree, the line-of-sight angle, or the head position of the driver. The facial information detecting unit 13 outputs the detected facial information to the driving capability estimating unit 15 and the facial expression estimating unit 16.

The physical information detecting unit 14 detects physical information related to the physical features of the driver on the basis of the face area detected by the face detecting unit 11 or the face parts detected by the face parts detecting unit 12. The physical information includes at least one of the heart rate, the heart rate variability, the heart rate interval (RRI), the brain wave, the pulse wave, the pulse rate variability, the blood pressure, the body temperature, or the sweat rate. Note that the physical information detecting unit 14 may detect the physical information using the face area or the face parts detected from the captured image of the imaging unit 2 or may detect the physical information using a detection result of a sensor (not illustrated). The physical information detecting unit 14 outputs the detected physical information to the driving capability estimating unit 15.

Note that the facial information is, of information related to biological functions, items regarded as facial features in physiology such as the face orientation angle, the eye opening degree, the blinking speed, the mouth opening degree, the line-of-sight angle, and the head position. The physical information is, of information related to biological functions, items regarded as physical features in physiology such as the heart rate, the heart rate variability, the RRI, the brain wave, the pulse wave, the pulse rate variability, the blood pressure, the body temperature, and the sweat rate.

The driving capability estimating unit 15 estimates the driving capability of the driver on the basis of at least one of the facial information detected by the facial information detecting unit 13 and the physical information detected by the physical information detecting unit 14. For example, the driving capability estimating unit 15 estimates a driving capability that corresponds to the facial information detected by the facial information detecting unit 13 and the physical information detected by the physical information detecting unit 14 using a model in which a correspondence relation among facial information and physical information of many and unspecified people in normal times and abnormal times and the driving capability are learned. Note that the driving capability estimating unit 15 may optimize the model for a driver of the host vehicle using facial information and physical information of the driver of the host vehicle. The driving capability has, for example, two levels of being capable and incapable. In a case of being capable of driving, the driver is in a condition suitable for driving, whereas in a case of being incapable of driving, the driver is in a condition unsuitable for driving or cannot drive. The driving capability estimating unit 15 outputs the driving capability that has been estimated to the emotion estimating unit 17.

The facial expression estimating unit 16 estimates the facial expression of the driver on the basis of the facial information detected by the facial information detecting unit 13. For example, the facial expression estimating unit 16 estimates a facial expression that corresponds to the facial information detected by the facial information detecting unit 13 on the basis of a predetermined correspondence relation between the facial information and the facial expression (so-called rule base). Alternatively, the facial expression estimating unit 16 may estimate a facial expression that corresponds to the facial information detected by the facial information detecting unit 13 using a model in which the correspondence relation between the facial information and the facial expression of many and unspecified people is learned (so-called machine learning). Further alternatively, the facial expression estimating unit 16 may estimate a facial expression by performing both the rule base and the machine learning. As for the facial expression, three types of facial expressions, for example, positive (smile), negative (glumly or crying), and neutral (other facial expressions) are set. The facial expression estimating unit 16 outputs the facial expression that has been estimated to the emotion estimating unit 17.

The emotion estimating unit 17 estimates the emotion of the driver represented by the degree of comfort and the degree of activeness on the basis of temporal changes in the driving capability estimated by the driving capability estimating unit 15 and temporal changes in the facial expression estimated by the facial expression estimating unit 16. Note that the "active" state in which the degree of activeness is high is a stale in which the driver is awake or sober, and the "inactive" state in which the degree of activeness is low is a stale in which the driver is sleeping or drunk.

Figure 2:
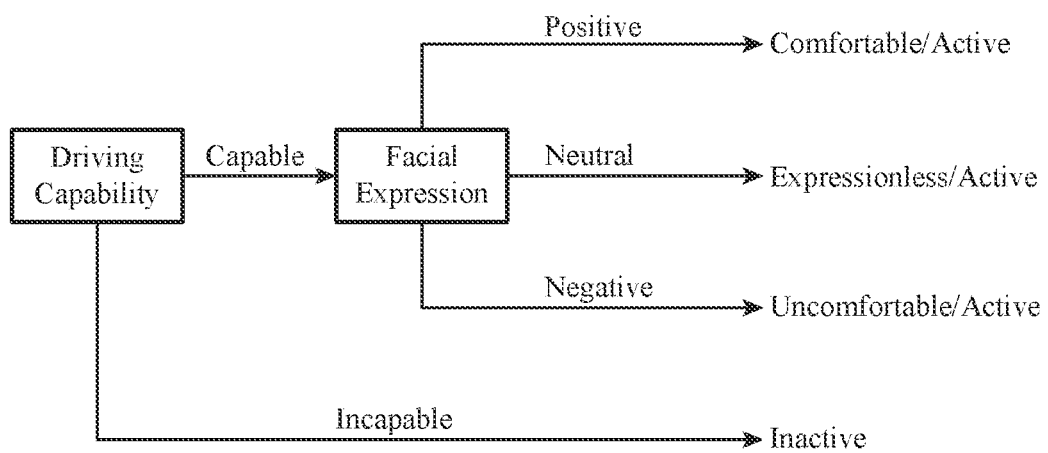
FIG. 2 is a diagram for explaining an emotion estimation method performed by an emotion estimating unit of the first embodiment.

FIG. 2 is a diagram illustrating an emotion estimation method by the emotion estimating unit 17 of the first embodiment.

In a case where the driver is incapable of driving, emotions are unlikely to be expressed in a facial expression, and it is difficult to estimate an emotion from the facial expression. Therefore, in a case where it is estimated by the driving capability estimating unit 15 that the driver is incapable of driving, the emotion estimating unit 17 determines the degree of activeness as being inactive.

On the other hand, in a case where it is estimated by the driving capability estimating unit 15 that the driver is capable of driving, the emotion estimating unit 17 determines the degree of activeness as being active. In addition, in a case where it is estimated by the driving capability estimating unit 15 that the driver is capable of driving, the emotion estimating unit 17 determines the degree of comfort as being comfortable when the facial expression estimated by the facial expression estimating unit 16 is positive, determines as being expressionless when the facial expression is neutral, and determines as being uncomfortable when the facial expression is negative.

In the following, an example of estimating emotions using the Russell's circumplex model will be described.

Figure 3:
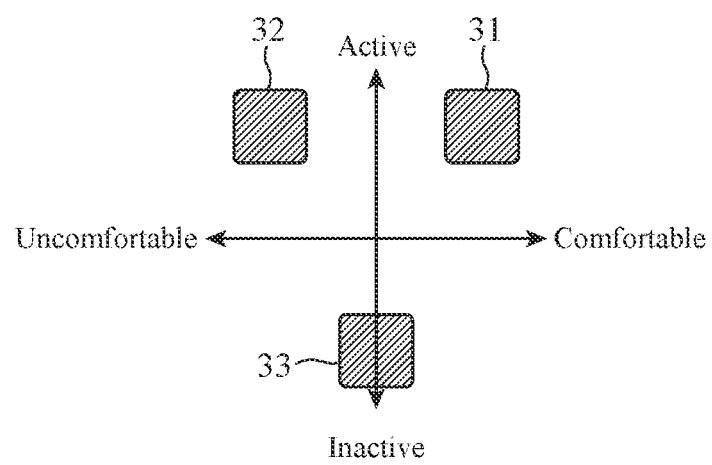
FIG. 3 is a graph for explaining the emotion estimation method performed by the emotion estimating unit of the first embodiment.

FIG. 3 is a graph for explaining the emotion estimation method by the emotion estimating unit 17 of the first embodiment. In the graph illustrated in FIG. 3, the vertical axis represents the degree of activeness, and the horizontal axis represents the degree of comfort. The emotion estimating unit 17 plots an emotion-expressing point on the graph of FIG. 3 depending on the degree of activeness and the degree of comfort determined on the basis of the driving capability and the facial expression. For example, in a case where the driving capability is "capable", the emotion estimating unit 17 moves the emotion-expressing point from the current position toward the active side by an amount that corresponds to the duration of being "capable". On the contrary, in a case where the driving capability is "incapable", the emotion estimating unit 17 plots an emotion-expressing point at the origin which is the intersection of the vertical axis and the horizontal axis and then moves the emotion-expressing point from the origin toward the inactive side by an amount that corresponds to the duration of being "incapable". Meanwhile, in a case where the facial expression is "positive", the emotion estimating unit 17 moves the emotion-expressing point from the current position toward the comfortable side by an amount that corresponds to the duration of being "positive". On the contrary, in a case where the facial expression is "negative", the emotion estimating unit 17 moves the emotion-expressing point from the current position toward the uncomfortable side by an amount that corresponds to the duration of being "negative". In a case where the facial expression is "neutral", the emotion estimating unit 17 moves the emotion-expressing point toward the origin by an amount that corresponds to the duration of being "neutral". Note that the amount of movement of the emotion-expressing point per unit time may be a value given in advance or a value different for each driver.

Moreover, in a case where an emotion-expressing point is plotted in an active and comfortable area 31 in the graph of FIG. 3, the emotion estimating unit 17 estimates the emotion of the driver as "excitement". The emotion estimating unit 17 estimates that the driver is gradually getting excited when the emotion-expressing point is moving toward the area 31. In a case where the driver is in an excited state, for example, overspeed is foreseen. In a case where an emotion-expressing point is plotted in an active and uncomfortable area 32, the emotion estimating unit 17 estimates the emotion of the driver as "discontent". The emotion estimating unit 17 estimates that the driver is gradually feeling discontent when the emotion-expressing point is moving toward the area 32. In a case where the driver is in a discontented state, for example, road rage is foreseen. In a case where an emotion-expressing point is plotted in an inactive area 33, the emotion estimating unit 17 estimates the emotion of the driver as "drowsiness". The emotion estimating unit 17 estimates that the driver is gradually getting drowsy when the emotion-expressing point is moving toward the area 33. If the driver is in a drowsy state, for example, dozing while driving is foreseen. Note that the types of emotions and the correspondence relation between areas and emotions in the graph of FIG. 3 are not limited to the above examples. Furthermore, the position and the size of the areas corresponding to emotions may be different for each driver.

Next, a specific example of emotion estimation will be described.

FIGS. 4A, 4B, and 4C are graphs each illustrating an example of temporal changes of an emotion estimated by the emotion estimating unit 17 of the first embodiment. In a case where the driving capability of the driver is "capable" and the facial expression is "positive", the emotion estimating unit 17 plots an emotion-expressing point 41 on a graph as illustrated in FIG. 4A. When the driving capability "capable" and the facial expression "positive" last, the emotion-expressing point 41 moves toward the active side and the comfortable side by the amount that corresponds to the duration. When the emotion-expressing point 41 moves to an emotion-expressing point 42 and approaches the area 31 as illustrated in FIG. 4B, the emotion estimating unit 17 can estimate the temporal change of the emotion such as that the driver is gradually getting excited.

In FIG. 4C, an emotion-expressing point 43 is plotted in the area 31 of excitement. In this case, when the driving capability "capable" and the facial expression "neutral" last, the emotion-expressing point 43 moves toward the origin by the amount that corresponds to the duration. Note that, in the first embodiment, the emotion estimating unit 17 gives priority to the facial expression "neutral" over the driving capability "capable" and thereby moves the emotion-expressing point 43. When the emotion-expressing point 43 moves to an emotion-expressing point 44 and moves away from the area 31 as illustrated in FIG. 4C, the emotion estimating unit 17 can estimate the temporal change of the emotion such as that the driver is gradually becoming calmed down.

Figure 5A:
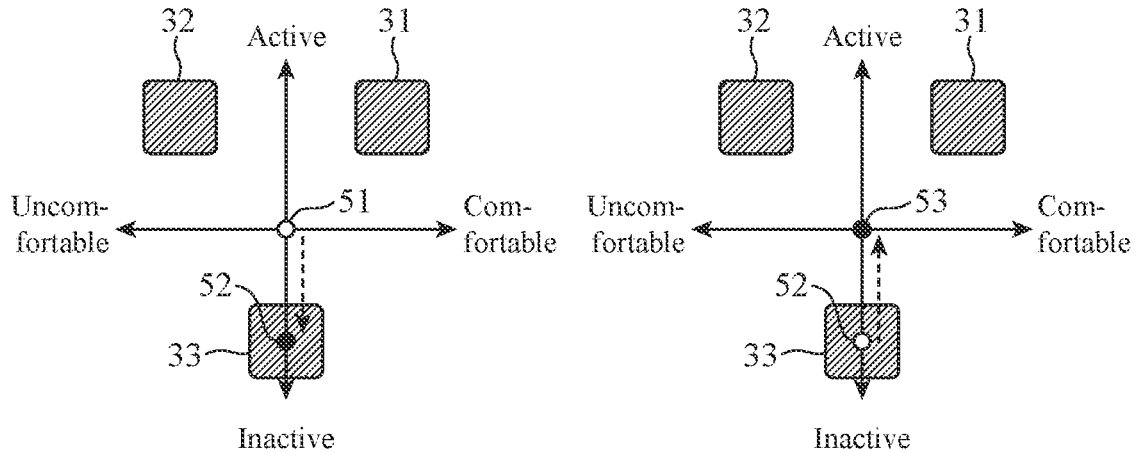
FIGS. 5A and 5B are graphs each illustrating another example of temporal changes of an emotion estimated by the emotion estimating unit of the first embodiment.
Figure 5B:
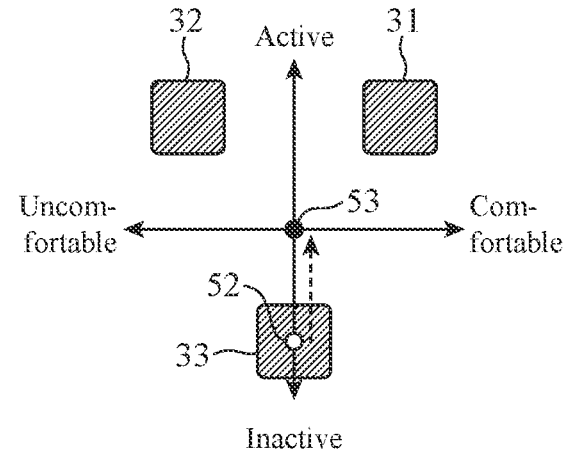

FIGS. 5A and 5B are graphs each illustrating another example of temporal changes of an emotion estimated by the emotion estimating unit 17 of the first embodiment. In a case where the driving capability of the driver is "incapable", the emotion estimating unit 17 plots an emotion-expressing point 51 at the origin regardless of the facial expression. Then, the emotion estimating unit 17 moves the emotion-expressing point 51 toward the inactive side by the amount that corresponds to the duration of the driving capability of "incapable". When the emotion-expressing point 51 moves to an emotion-expressing point 52 and approaches the area 33 as illustrated in FIG. 5A, the emotion estimating unit 17 can estimate the temporal change of the emotion such as that the driver is gradually getting drowsy.

In a case where the driving capability of the driver becomes "capable", the emotion estimating unit 17 moves the emotion-expressing point 52 to the active side by the amount that corresponds to the duration of the driving capability of "capable". When the emotion-expressing point 52 moves to an emotion-expressing point 53 and moves away from the area 33 as illustrated in FIG. 5B, the emotion estimating unit 17 can estimate the temporal change of the emotion such as that the driver is gradually awakening. Note that, in FIG. 5B, an example in which the driving capability is "capable", and the facial expression is "neutral" is illustrated, and thus the emotion-expressing point 52 moves toward the origin. In a case where the facial expression is "positive" (or "negative"), the emotion-expressing point 52 moves toward the active side and the comfortable side (or the uncomfortable side).

Next, the operation of the emotion estimation device 1 will be described.

Figure 6:
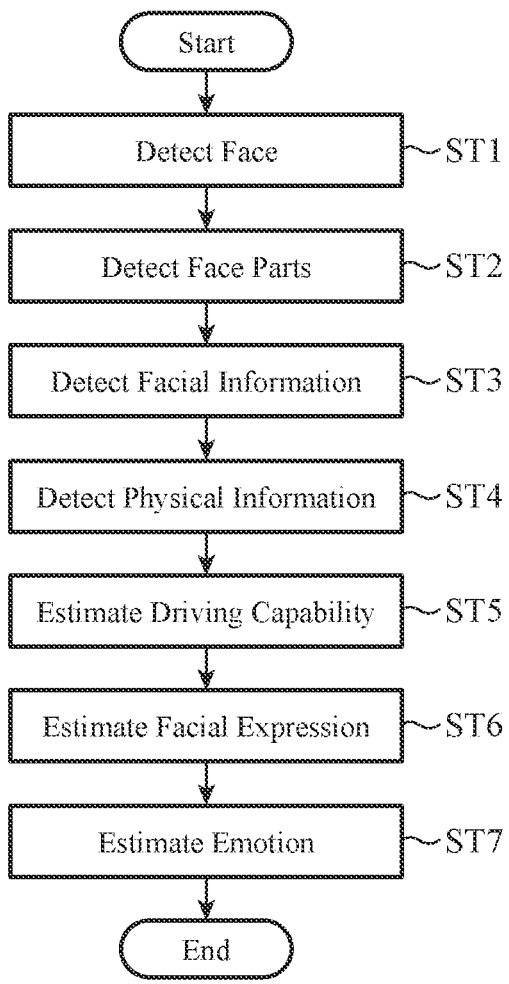
FIG. 6 is a flowchart illustrating an example of the operation of the emotion estimation device according to the first embodiment.

FIG. 6 is a flowchart illustrating an example of the operation of the emotion estimation device 1 according to the first embodiment. For example, when the ignition switch of the vehicle is turned on, the emotion estimation device 1 initiates the operation illustrated in the flowchart of FIG. 6 and repeats this operation until the ignition switch is turned off.

In step ST1, the face detecting unit 11 detects the face area of the driver from the captured image of the imaging unit 2, in step ST2, the face parts detecting unit 12 detects face parts from the face area in the captured image. Note that, as described above, the functions of the face detecting unit 11 and the face parts detecting unit 12 may be included in an external device. In such a configuration, the emotion estimation device 1 does not perform the operation in step ST1 nor ST2.

In step ST3, the facial information detecting unit 13 detects facial information related to the facial features of the driver on the basis of the face parts. In step ST4, the physical information detecting unit 14 detects physical information related to the physical features of the driver on the basis of the face area or the face parts in the captured image. In step ST5, the driving capability estimating unit 15 estimates the driving capability of the driver on the basis of the facial information and the physical information. In step ST6, the facial expression estimating unit 16 estimates the facial expression of the driver on the basis of the facial information. In step ST7, the emotion estimating unit 17 estimates an emotion represented by the degree of comfort and the degree of activeness on the basis of temporal changes in the driving capability and the facial expression of the driver.

The operation of the emotion estimation device 1 illustrated in the flowchart of FIG. 6 is merely an example, and it is not limited to this operation. For example, in a case where the physical information detecting unit 14 detects the physical information using only the face area without using the face parts, the face parts detecting unit 12 does not perform the operation related to the face parts detection of step ST2. Further, for example, in a case where the driving capability estimating unit 15 and the facial expression estimating unit 16 estimate the driving capability using only the facial information detected by the facial information detecting unit 13, the physical information detecting unit 14 does not perform the operation related to the physical information detection of step ST4.

As described above, the emotion estimation device 1 according to the first embodiment includes the facial information detecting unit 13, the physical information detecting unit 14, the driving capability estimating unit 15, the facial expression estimating unit 16, and the emotion estimating unit 17. The facial information detecting unit 13 detects facial information related to facial features of a driver of the vehicle. The physical information detecting unit 14 detects physical information related to physical features of the driver. The driving capability estimating unit 15 estimates the driving capability of the driver on the basis of the facial information and the physical information. The facial expression estimating unit 16 estimates the facial expression of the driver on the basis of the facial information. The emotion estimating unit 17 estimates the emotion of the driver represented by the degree of comfort and the degree of activeness on the basis of temporal changes in the driving capability of the driver and the facial expression of the driver. With this configuration, the emotion estimation device 1 is not only capable of estimating the emotion of the driver at a certain point in time but also estimating an emotion in consideration of temporal changes such as that the driver is gradually getting excited or gradually becoming calmed down.

The emotion estimating unit 17 of the first embodiment estimates the emotion of the driver on the basis of a duration of the facial expression of the driver in a case where it is estimated by the driving capability estimating unit 15 that the driver is capable of driving. As a result, the emotion estimating unit 17 can accurately estimate the emotion even when the driver's state is such that the emotion is hard to appear in the facial expression.

Furthermore, the emotion estimating unit 17 of the first embodiment determines the degree of comfort and the degree of activeness depending on the duration of the driving capability of the driver and the duration of the facial expression of the driver and estimates the emotion of the driver that corresponds to the degree of comfort and the degree of activeness that have been determined by referring to a predetermined correspondence relation among the degree of comfort, the degree of activeness, and emotions.

As a result, the emotion estimating unit 17 can easily estimate an emotion in consideration of the temporal changes as illustrated in FIGS. 3 to 5.

Second Embodiment

Figure 7:
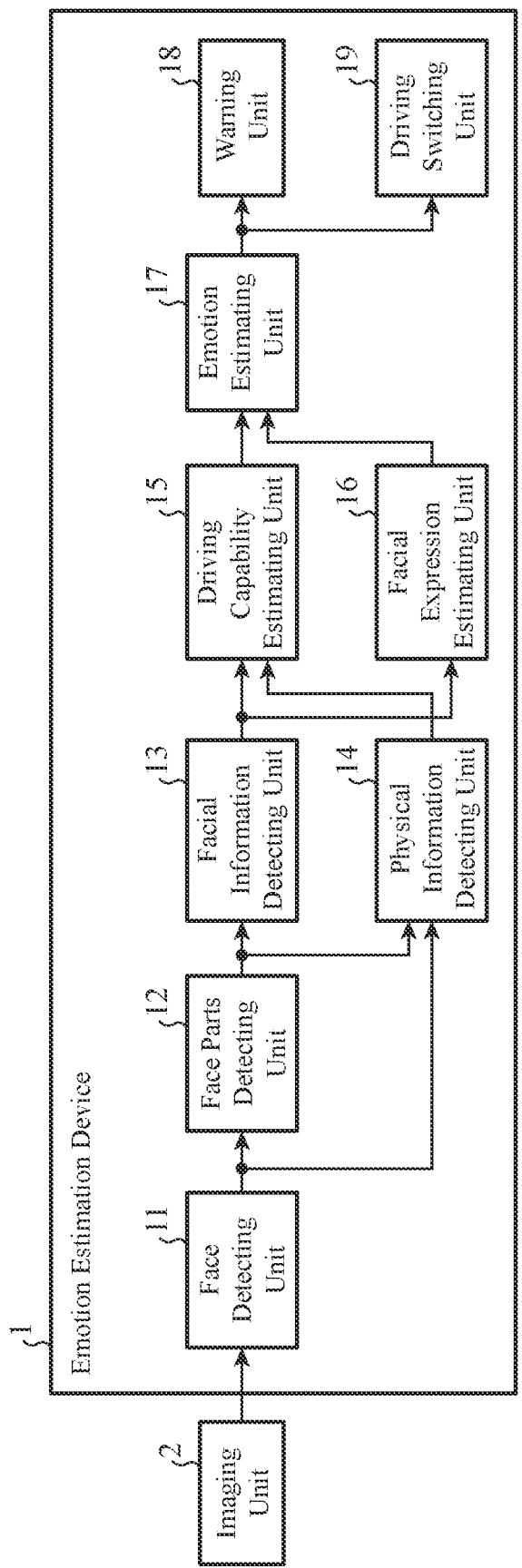
FIG. 7 is a block diagram illustrating an exemplary configuration of an emotion estimation device according to a second embodiment.

FIG. 7 is a block diagram illustrating an exemplary configuration of an emotion estimation device 1 according to a second embodiment. The emotion estimation device 1 according to the second embodiment has a configuration in which a warning unit 18 and a driving switching unit 19 are added to the emotion estimation device 1 of the first embodiment illustrated in FIG. 1. In FIG. 7, the same or a corresponding component as that in FIG. 1 is denoted by the same symbol, and description thereof is omitted.

The warning unit 18 includes at least one of a display or a speaker. The warning unit 18 warns the driver or prompts switching from manual driving to autonomous driving depending on the emotion estimated by the emotion estimating unit 17. For example, when the driver gradually gets excited and an emotion-expressing point enters the area 31 of FIG. 3, for example, overspeed is foreseen. Therefore, the warning unit 18 warns the driver by displaying a warning screen on the display or outputting a warning sound from the speaker. Alternatively, when the driver gradually feels discontented and an emotion-expressing point enters the area 32 of FIG. 3, for example, road rage is foreseen. Therefore, the warning unit 18 warns the driver by displaying a warning screen on the display or outputting a warning sound from the speaker. Further alternatively, when the driver gradually feels drowsy and an emotion-expressing point enters the area 33 of FIG. 3, for example, dozing while driving is foreseen. Therefore, the warning unit 18 warns the driver by displaying a warning screen on the display or outputting a warning sound from the speaker.

Note that the warning unit 18 may end the display of the warning screen when a certain period of time has passed after the warning screen has been displayed or may end the display of the warning screen when the driver becomes calmed down from a state of excitement or discontent or awakens from a state of drowsiness. Similarly, the warning unit 18 may end the output of the warning sound when a certain period of time has passed after the warning sound has been output or may end the output of the warning sound when the driver becomes calmed down from a state of excitement or discontent or awakens from a state of drowsiness.

Moreover, when the driver gradually feels drowsy and the emotion-expressing point enters the area 33 of FIG. 3, the warning unit 18 may display, on a display, a screen prompting switching to autonomous driving or may output, from a speaker, voice prompting switching to autonomous driving.

Furthermore, the emotion estimation device 1 may automatically perform switching from manual driving to autonomous driving when the driver feels drowsy. Specifically, the driving switching unit 19 instructs a vehicle control device (not illustrated) to switch from manual driving to autonomous driving when the driver gradually feels drowsy and the emotion-expressing point enters the area 33 of FIG. 3.

As described above, the emotion estimation device 1 according to the second embodiment includes the warning unit 18. The warning unit 18 warns the driver or prompts switching to autonomous driving depending on the emotion of the driver estimated by the emotion estimating unit 17. As a result, the emotion estimation device 1 can warn at appropriate timing depending on the emotion of the driver.

Lastly, the hardware configuration of the emotion estimation devices 1 of the embodiments will be described.

Figure 8:
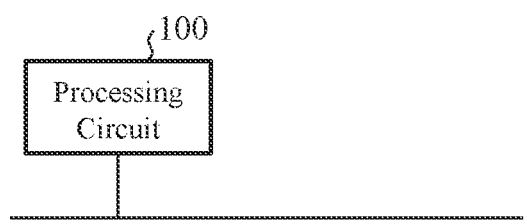
FIG. 8 is a diagram illustrating an example of the hardware configuration of the emotion estimation devices of each of the embodiments.
Figure 9:
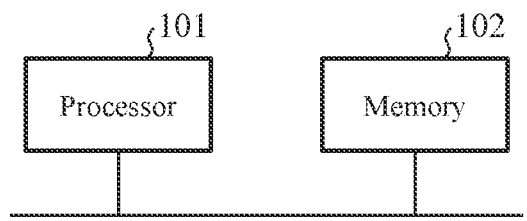
FIG. 9 is a diagram illustrating another example of the hardware configuration of the emotion estimation devices of each of the embodiments.

FIGS. 8 and 9 are diagrams each illustrating a hardware configuration example of the emotion estimation device 1 of each of the embodiments. The functions of the face detecting unit the face parts detecting unit 12, the facial information detecting unit 13, the physical information detecting unit 14, the driving capability estimating unit 15, the facial expression estimating unit 16, the emotion estimating unit 17, the warning unit 18, and the driving switching unit 19 in the emotion estimation device 1 are implemented by a processing circuit. That is, the emotion estimation device 1 includes a processing circuit for implementing the above functions. The processing circuit may be a processing circuit 100 as dedicated hardware or may be a processor 101 for executing a program stored in a memory 102.

In the case where the processing circuit is dedicated hardware as illustrated in FIG. 8, the processing circuit 100 corresponds to, for example, a single circuit, a composite circuit, a programmed processor, a parallel programmed processor, an application specific integrated circuit (ASIC), a field-programmable gate array (FPGA), or a combination thereof. The functions of the face detecting unit 11, the face parts detecting unit 12, the facial information detecting unit 13, the physical information detecting unit 14, the driving capability estimating unit 15, the facial expression estimating unit 16, the emotion estimating unit 17, the warning unit 18, and the driving switching unit 19 may be implemented by a plurality of processing circuits 100, or the functions of the respective units may be collectively implemented by a single processing circuit 100.

As illustrated in FIG. 9, in a case where the processing circuit is the processor 101, the functions of the face detecting unit 11, the face parts detecting unit 12, the facial information detecting unit 13, the physical information detecting unit 14, the driving capability estimating unit 15, the facial expression estimating unit 16, the emotion estimating unit 17, the warning unit 18, and the driving switching unit 19 are implemented by software, firmware, or a combination of software and firmware. The software or the firmware is described as a program, which is stored in the memory 102. The processor 101 reads and executes a program stored in the memory 102 and thereby implements the functions of the above units. That is, the emotion estimation device 1 includes the memory 102 for storing the program, execution of which by the processor 101 results in execution of the steps illustrated in the flowchart of FIG. 6. In addition, it can be said that this program causes a computer to execute the procedures or the methods performed in the face detecting unit the face parts detecting unit 12, the facial information detecting unit 13, the physical information detecting unit 14, the driving capability estimating unit 15, the facial expression estimating unit 16, the emotion estimating unit 17, the warning unit 18, and the driving switching unit 19.

Here, the processor 101 refers to, for example, a central processing unit (CPU), a processing device, an arithmetic device, or a microprocessor.

The memory 102 may be a nonvolatile or volatile semiconductor memory such as a random access memory (RAM), a read only memory (ROM), an erasable programmable ROM (EPROM), or a flash memory, a magnetic disk such as a hard disk or a flexible disk, or an optical disk such as a compact disc (CD) or a digital versatile disc (DVD).

Note that some of the functions of the face detecting unit 11, the face parts detecting unit 12, the facial information detecting unit 13, the physical information detecting unit 14, the driving capability estimating unit 15, the facial expression estimating unit 16, the emotion estimating unit 17, the warning unit 18, and the driving switching unit 19 may be implemented by dedicated hardware, and some may be implemented by software or firmware. In this manner, the processing circuit in the emotion estimation device 1 can implement the above functions by hardware, software, firmware, or a combination thereof.

Note that the present invention may include a flexible combination of the embodiments, a modification of any component of the embodiments, or omission of any component in the embodiments within the scope of the present invention.

INDUSTRIAL APPLICABILITY

An emotion estimation device according to the present invention is suitable for an emotion estimation device for estimating an emotion of a driver, a passenger, or the like who has boarded a mobile object including a vehicle, a train, a ship, or an aircraft.

REFERENCE SIGNS LIST

1: emotion estimation device, 2: imaging unit, 11: face detecting unit, 12: face parts detecting unit, 13: facial information detecting unit, 14: physical information detecting unit, 15: driving capability estimating unit, 16: facial expression estimating unit, 17: emotion estimating unit, 18: warning unit, 19: driving switching unit, 31 to 33: area, 41 to 44, 51 to 53: emotion-expressing point, 100: processing circuit, 101: processor, 102: memory

The invention claimed is:

1. An emotion estimation device comprising processing circuitry
   to detect facial information related to a facial feature of a driver of a vehicle,
   to detect physical information related to a physical feature of the driver,
   to estimate driving capability of the driver on a basis of the facial information and the physical information,
   to estimate a facial expression of the driver as one from among a positive facial expression, a negative facial expression, and a neutral facial expression on a basis of the facial information, and
   to estimate an emotion of the driver represented by a degree of comfort and a degree of activeness on a basis of a temporal change in the driving capability of the driver and the facial expression of the driver.

2. The emotion estimation device according to claim 1, wherein the processing circuitry estimates the emotion of the driver on a basis of a duration of the facial expression of the driver in a case where it is estimated that the driver is capable of driving.

3. The emotion estimation device according to claim 1, wherein the processing circuitry determines the degree of comfort and the degree of activeness depending on a duration of the driving capability of the driver and the duration of the facial expression of the driver and estimates the emotion of the driver that corresponds to the degree of comfort and the degree of activeness that have been determined by referring to a predetermined correspondence relation among the degree of comfort, the degree of activeness, and the emotion.

4. The emotion estimation device according to claim 1, wherein the processing circuitry is further configured to warn the driver or to prompt the driver to switch to autonomous driving depending on the emotion of the driver estimated.

5. The emotion estimation device according to claim 1, wherein the estimation of the emotion of the driver comprises:
   assigning a first number value to the driving capability of the driver; assigning a second number value to the facial expression of the driver;
   gradually increasing or decreasing at least one of the first number value and the second number value based on the temporal change in the driving capability of the driver and the temporal change in the facial expression of the driver; and
   estimating the emotion of the driver based on the first number value and the second number value.

6. The emotion estimation device according to claim 5, wherein the processing circuitry is configured to estimate the emotion of the driver from among a plurality of emotions, each of the plurality of emotions corresponding to a respective region in a graph in which one axis represents the driving capability of the driver and another axis represents the facial expression of the driver.

7. The emotion estimation device according to claim 1, wherein at least one of the degree of comfort and the degree of activeness is changed by an amount that corresponds to a duration of any one of the positive facial expression, the negative facial expression, or the neutral facial expression of the driver.

8. An emotion estimation method performed by processing circuitry comprising:
   detecting facial information related to a facial feature of a driver of a vehicle;
   detecting physical information related to a physical feature of the driver;
   estimating driving capability of the driver on a basis of the facial information and the physical information;
   estimating a facial expression of the driver as one from among a positive facial expression, a negative facial expression, and a neutral facial expression on a basis of the facial information; and
   estimating an emotion of the driver represented by a degree of comfort and a degree of activeness on a basis of a temporal change in the facial expression of the driver in a case where it is estimated that the driver is capable of driving.

* * * * *